(12) United States Patent
Werner

(10) Patent No.: US 10,363,076 B2
(45) Date of Patent: Jul. 30, 2019

(54) BONE FASTENING SYSTEM

(71) Applicant: Clement Max Leonard Werner, Mannedorf (CH)

(72) Inventor: Clement Max Leonard Werner, Mannedorf (CH)

( * ) Notice: Subject to any disclaimer, the term of this patent is extended or adjusted under 35 U.S.C. 154(b) by 131 days.

(21) Appl. No.: 15/119,257

(22) PCT Filed: Feb. 16, 2015

(86) PCT No.: PCT/IB2015/051130
§ 371 (c)(1),
(2) Date: Aug. 16, 2016

(87) PCT Pub. No.: WO2015/125056
PCT Pub. Date: Aug. 27, 2015

(65) Prior Publication Data
US 2017/0007306 A1  Jan. 12, 2017

(30) Foreign Application Priority Data
Feb. 18, 2014  (EP) .................................... 14000579

(51) Int. Cl.
*A61B 17/86* (2006.01)
*A61B 17/88* (2006.01)
(Continued)

(52) U.S. Cl.
CPC ...... *A61B 17/8685* (2013.01); *A61B 17/7055* (2013.01); *A61B 17/7098* (2013.01); *A61B 17/809* (2013.01); *A61B 17/8042* (2013.01); *A61B 17/8066* (2013.01); *A61B 17/864* (2013.01); *A61B 17/8695* (2013.01);
(Continued)

(58) Field of Classification Search
CPC . A61B 17/86; A61B 17/8685; A61B 17/8695; A61B 17/88; A61B 17/8875
See application file for complete search history.

(56) References Cited

U.S. PATENT DOCUMENTS 2,489,868 A   11/1949 Dowling et al.
5,601,550 A   2/1997  Esser
(Continued)

FOREIGN PATENT DOCUMENTS

EP  1417935          5/2004
WO  2007109140 A2    9/2007
(Continued)

*Primary Examiner* — Christopher J Beccia
(74) *Attorney, Agent, or Firm* — Allen, Dyer, Doppelt + Gilchrist, P.A.

(57) ABSTRACT

A bone fastening system may include a cannulated screw component, a seating component, and a holding component. The screw component may include a screw head arranged in the region of a proximal end of the screw component, and an elongate screw shaft extending from the screw head along a longitudinal axis towards a distal end of the screw component. The screw head may include a proximal surface on a front side facing the proximal end and a distal surface on a back side facing the distal end. A portion of the distal surface may form a contact surface. The seating component may include a central opening having an opening diameter larger than the maximum diameter of the screw shaft and smaller than the maximum diameter of the screw head.

14 Claims, 7 Drawing Sheets

(51) Int. Cl.
  *A61B 17/70*    (2006.01)
  *A61B 17/80*    (2006.01)
  A61B 17/68      (2006.01)
  A61B 17/90      (2006.01)

(52) U.S. Cl.
  CPC ...... *A61B 17/8875* (2013.01); *A61B 17/8897* (2013.01); *A61B 17/7064* (2013.01); *A61B 2017/681* (2013.01); *A61B 2017/90* (2013.01)

(56) References Cited

U.S. PATENT DOCUMENTS

| | | | |
|---|---|---|---|
| 5,879,389 A | 3/1999 | Koshino | |
| 2002/0143338 A1 | 10/2002 | Orbay et al. | |
| 2008/0306555 A1* | 12/2008 | Patterson | A61B 17/8695 606/303 |
| 2012/0010662 A1* | 1/2012 | O'Neil | A61B 17/7064 606/279 |
| 2012/0191191 A1* | 7/2012 | Trieu | A61B 17/683 623/17.11 |
| 2012/0316608 A1 | 12/2012 | Foley | |
| 2013/0267836 A1 | 10/2013 | Mauldin et al. | |
| 2013/0296942 A1 | 11/2013 | Michelson | |

FOREIGN PATENT DOCUMENTS

| | | |
|---|---|---|
| WO | 2011068818 | 6/2011 |
| WO | 2012009162 | 1/2012 |
| WO | 2012062272 A2 | 5/2012 |

\* cited by examiner

BONE FASTENING SYSTEM

TECHNICAL FIELD

The present invention further relates to the use of the bone fastening system for the treatment of a pelvic pathology and to a method for inserting the bone fastening system into the pelvic ring.

BACKGROUND

Such internal fixation devices allow for fixating the fractured joint or bone parts in their correct position and thereby promote healing of the fracture. In order to keep the damage to surrounding tissues as low as possible, less invasive methods of fracture stabilization are now more popular than ever and the development and application of minimally invasive and percutaneous fixation techniques have seen a great deal of interest in recent years.

The same revolution is taking place in pelvic fracture management. The sacro-iliac (SI) articulation is one of the most complex joints orthopedic surgeons to deal with since the anatomy of the sacrum and surrounding structures make diagnosis and fixation difficult.

One way to fix injuries of the pelvic ring is described in U.S. Pat. No. 5,601,550, for instance, which relates to a pelvic drill guide apparatus that is used to insert external fixation pins into a patient's pelvis that is fractured in "open book" fracture fashion. Multiple fixation pins are placed into the pelvis on each side and an external fixation frame holds the pins, and, thus the pieces of the pelvis together. The primary disadvantages of such external fixation of pelvic fractures include high risk of pin tract infections and highly impaired motion range of the patient due to the external frame.

Whereas open treatment of pelvic fractures as addressed in U.S. Pat. No. 5,601,550 predominated just a few years ago, today, open methods are giving way to newer techniques of minimal invasive procedures, e.g. closed or limited open reduction, coupled with percutaneous stabilization.

Internal bone fixation means are described in U.S. Pat. No. 2,489,868, for instance. The document relates to a bone fastening device for rigidly and fixedly fastening bone parts together. However, although numerous different approaches for internal bone fixation have been developed, choices of suitable screws and surgical tools for use in treatment of pelvic ring fractures are still very limited.

One complication associated with internal bone fixation, and in particular joint fixation, is migration of the screw over time owing to normal physiologic movement and remodeling of the bone. Depending on the bone density and structure, the screws either tend to migrate out of the bone, leading to loosening of the screw, or to migrate into the bone, which significantly complicates removal of the screws after the fracture has healed. The risk of migration of bone screws into the bone can be reduced by the use of washers which provide an increased retention surface and can further provide a compressive force on the bone region. However, the benefits provided by the washer are partly offset by the difficulty to remove the washer together with the screw later-on after the injury has healed. In the worst case, the washer forms a strong attachment to the bone, whereas the screw loosens and migrates out of the bore. This not only impairs the fixation of the fracture but also complicates removal of both, the migrated screw and the attached washer from the body.

To address this problem, fixed screw-washer assemblies have been described in the art. WO 2007/109140, for instance, relates to a screw assembly for insertion into a bone region. The screw comprises a proximal threaded area, which engages with a threaded area of the washer to fixedly secure the washer to the screw body. One drawback of such assemblies is that due to the increased friction surface provided by the washer, a greater amount of torque is required to be applied to the screw during fastening, which reduces the ease of operation and can damage the screw.

SUMMARY

Loosening and migration of bone screws is exacerbated inter alia by inadequate primary position of the screw. However, ideal positioning of a screw in the pelvic region is particularly difficult due to the complex anatomy and hard-to-access areas of the pelvis, especially of the posterior pelvic ring. In order to increase precision of screw positioning, various techniques for CT-guided/computer-navigated screw positioning have been described. Yet, in the emergency room (ER) with patients in urgent need for early primary care, these time-consuming techniques are unsuitable.

It is therefore an object of the present invention to provide a bone fastening system for accurate stabilization of an articulated joint or a bone fracture, in particular of pelvic ring fractures, that provides increased screw migration resistance and at the same time allows for secure removal of all components of the bone fastening system after the healing process is complete. It is a further object of the present invention to provide a straight-forward and accurate method for inserting the bone fastening system for stabilizing fractures of the pelvic ring.

The bone fastening system of the present invention comprises a cannulated screw component and a seating component. The screw component comprises a screw head arranged in the region of a proximal end of the screw component, and an elongate screw shaft extending from the screw head along a longitudinal axis towards a distal end of the screw component.

The screw head comprises a proximal surface on a front side facing the proximal end and a distal surface on a back side facing the distal end. At least a portion of the distal surface forms a contact surface.

The seating component comprises a central opening, a seating surface and a bottom surface. The central opening has an opening diameter which is larger than the maximum diameter of the screw shaft and which is smaller than the maximum diameter of the screw head. The seating surface is intended for abutting against the contact surface and the bottom surface is intended for abutting against the bone when the bone fasting system is in a fully engaged state.

The bone fastening system further comprises a holding component, which is connectable or integrally formed with the seating component. Together with the seating component, the holding component defines an accommodation portion for accommodating the screw head such that the screw component and the seating component are connected in a non-detachable manner while at the same time allowing axial rotation of the seating component with respect of the screw component.

The bone fastening system of the present invention is particularly well suited for use in the treatment of bone fractures. The cannulated screw component comprises a central bore extending the entire length of the screw component along the longitudinal axis and provides interfragmentary compression and high stability across the fracture. In addition it allows for using guide wire which is a major facilitator of minimally invasive surgery.

Thanks to the screw component and a seating component being non-detachably fixed to each other, both parts can be handled as one unit without losing one part. In particular, the screw component and the seating component can easily be removed after fracture healing without risking that one component remains attached to the bone after removal.

The term "non-detachably" as used in the context of the present invention is to be interpreted in terms of two parts being connected to each other such that they are not separated by forces which are normally subjected to the bone fastening system under normal use. In particular, the connection between the two parts fixed to each other does not break under normal stresses acting on the bone fastening system in the implanted state and allows for conjoint removal of both parts from the body. An example of a non-detachable connection can be established by welding two parts together.

In line with the present invention, the seating component and the holding component define an accommodation portion for accommodating the screw head. In the context of the present invention this means that the screw head is at least partly surrounded by the accommodation portion. Nevertheless, the screw head can freely rotate around the longitudinal axis relative to the seating component. This has the effect that the seating component does not apply additional rotational resistance to the screw component and avoids that an increased amount of torque needs to be applied to the screw during fastening. At the same time, the bone fastening system of the present invention decreases the risk of migration of the screw component and/or the seating component.

As mentioned above, the bone fastening system of the present invention comprises a cannulated screw component, a seating component and a holding component.

In general, the screw shaft is cylindrically shaped and of constant diameter. Nevertheless, in some cases it might be preferred to have a screw component with a shaft of variable diameter, e.g. with conically shaped shaft widening from the tip towards the head.

The shaft normally has a smaller diameter than the screw head and has an outer thread for screwing the screw into a bone. The thread may be of a self-tapping kind that does not require a thread being pre-cut into the bone.

The outer diameter of the seating component may vary depending upon the needs and desires of the particular bone structure. Thus, the seating or bottom surface may have an irregular or non-circular shape.

For permitting stable abutment against each other, the contact surface and the seating surface are generally of matching contour, e.g. co-planar.

In a preferred embodiment, the screw component remains rotatable with respect to the seating component during insertion of the screw component until the screw component is fully inserted, i.e. until the seating component is pressed against the bone by the screw head.

In a preferred embodiment, the holding component comprises a holding surface, which is intended to abut and at least partially overlaps with the proximal surface of the screw head when viewed in longitudinal direction. By the at least partial overlap of the holding surface and the proximal surface of the screw head, the screw head can be safely accommodated in the accommodation portion.

In a further preferred embodiment, not only the seating component but also the holding component comprises or defines a central opening having an opening diameter smaller than the maximum diameter of the screw head. In this case, the diameter of the central opening of the seating component and of the holding component, respectively, is restricted such that the screw head may not pass through without deforming or breaking at least one of the components, i.e. the screw head or the seating component and/or the holding component, respectively. The diameter of the central opening of the holding component is preferably sized to allow insertion of surgical instruments, e.g. a screwdriver, for engaging with the screw component.

In a preferred embodiment, the seating component and/or the holding component is elastically deformable, at least in a region around their respective central opening, to allow the diameter of the respective central opening to be widened sufficiently for the screw head to pass through. Thus, the ability of the seating component and/or the holding component to deform in order to change the diameter of their central opening allows for insertion of the screw head from below through the central opening of the seating component and/or from above through the central opening of the holding component into the accommodation portion. It is in this case preferred that the screw head is formed of a harder material than the holding component and/or the seating component, at least in the elastically deformable region, to facilitate insertion of the screw head through the respective central opening. After the screw head having passed the respective central opening, the holding component and/or the seating component preferably returns to its original shape and the screw head cannot be removed from the accommodation portion unless force is again applied to deform the holding component and/or the seating component.

In a further preferred embodiment, the holding component is integrally formed with the seating component. In this embodiment the holding component and the seating component are therefore formed in a continuous material formation, meaning as one piece. The connection of the holding component and the seating component is thus non-releasable and highly stable. In addition, being formed as one piece avoids the formation of micro-gaps in which bacteria may propagate.

In an exemplary embodiment, the holding component consists of a multiplicity of integrally formed elastically deformable fingers, which protrude from the seating surface of the seating component and are evenly distributed around the central opening of the latter. The fingers preferably match the outer contour of the screw head, by being slightly arc-shaped, for instance, and define the accommodation portion for the screw head. The fingers comprise finger tips, which are preferably tilted towards the axial center axis of the seating component to define a central opening of the holding component. As the screw head is pushed through the central opening of the holding component during assembly, the fingers are deformed or deflected radially outwards, i.e. away from the axial center axis until the diameter of the central opening is sufficiently widened to allow the screw head to pass through and to be received within the accommodation portion. After the screw head has passed through the central opening, the fingers spring back inwards toward the center of the opening. In order to hold the screw head within the accommodation portion, preferably at least the finger tips are substantially co-planar with the proximal surface of the screw head. Nevertheless, once the screw head is retained within the accommodation portion, the fingers or the finger tips do act radially on the proximal surface of the screw head but allow for axial rotation of the screw component with respect of the seating component.

In an alternative preferred embodiment the holding component is in the form of an end cap that is releasably connected to the seating component. The shape and dimensions of the cap are in this case preferably adapted to the outer contour and size of the screw head. In particular, the inner contour of the cap and the outer contour of the screw head are preferably matched such that they have e.g. a common inclination.

For releasably connecting the end cap to the seating component the end cap preferably comprises a threaded section for engagement with a correspondingly threaded section of the seating component. The seating component and the end cap can thereby be screwed together, which provides a straight-forward and strong connection.

It is further preferred that the bone fastening system is designed such that, when it is brought into the fully engaged state, the seating component is fixed to the screw component in a manner to prevent relative longitudinal displacement. Thus, at least part of the contact surface of the screw head abuts against the seating surface and the holding surface at least partly abuts the proximal surface of the screw head.

In a preferred embodiment the seating component comprises protrusions extending from the bottom surface. The protrusions may be in the form of teeth, serrations, grooves, or ridges and are intended for grabbing into the bone, holding the bone fastening system in place. This prevents migration of both, the screw component and the seating component.

In a preferred embodiment the bone fastening system preferably comprises an axial channel extending along the longitudinal axis through the screw head and the screw shaft and opening out into the exterior through a primary fenestration arranged at the distal end of the screw component. This allows for the injection of bone cement through the screw component into the cancellous bone to augment the bone around the screw threads in order to increase the strength of fixation of the screw in the bone and to fill the fracture void. Augmentation with bone cement has also shown to reduce the risk for screw loosening. In addition, cement formulations with antibiotics or osteoinductive proteins can be introduced if there are indications of inflammation or osteoporosis.

The channel preferably further opens out into at least one secondary fenestration arranged offset from the distal end at a predetermined height of the screw shaft. Through the secondary fenestration injection of bone cement in the area around the screw threads is facilitated and allows simple, accurate and timely cement augmentation after insertion.

It is further preferred that the screw head comprises a torque receiving surface intended to receive torque from an insertion tool. The torque receiving surface may be in formed in a central depression or slits in the proximal surface of the screw head. At least a section of this depression may have a non-circular symmetric circumference, such as a hexagonal or torx shape. Standard EN DIN ISO 10664 describes a corresponding internal torx for screws and is hereby incorporated by reference. The torque receiving surface can thus be engaged by a screwdriver to rotate the screw. Alternatively, the torque receiving surface may be formed on the outer surface of a post protruding from the proximal surface of the screw component. The post may have a polygonal cross-section, e.g. in the shape of a hexagon, octagon or a torx.

With regard to the dimensions of the bone fastening system, the screw shaft has preferably a diameter ranging from 7.0 to 8.0 mm, more preferably ranging from 7.2 to 7.5 mm.

The length of the screw component is preferably ranging from 20 to 200 mm, preferably from 68 to 180 mm. A screw component in this range allows for stable fixation of larger bone fragments, such as the pelvic ring.

In a preferred embodiment, the bone fastening system further comprises a counterpart with a threaded nut that fits the distal end of the screw thread for transiliac fixation. The counterpart is preferably disc-shaped such that an additional compression force may be exerted on the bone.

The components of the bane fastening system can be prepared from any biologically acceptable materials suitable for medical applications, including metals and ceramics. It goes without saying that the components can be made from different materials or all from the same material. Examples of preferred materials are commercially pure titanium, titanium alloys, cobalt-chrome alloys, stainless steel alloys, super-elastic metallic alloys and ceramic materials. The components of the bone fastening system may also be fabricated from a combination of two or more of the above-described materials.

In a preferred embodiment, the components of the bone fastening system consist of titanium, a titanium alloy or stainless steel. These materials are particularly well suited, since they demonstrate sufficient stability for application in the field of bone fastening and can also be brought into the desired shape without difficulty. In addition, components made of these materials can be easily cleaned and sterilized, which is vital for application in surgical procedures in order to prevent infections and other undesirable side effects.

The bone fastening system of the present invention is preferably employed in the treatment of a pelvic pathology and more preferably in the treatment of a degenerative disease of the iliosacral joint requiring stabilization and/or the fracture management of the pelvic ring, in particular high energy fracture of the pelvic ring, iliosacral joint disruption and associated pelvic fracture, osteoporotic fracture of the sacrum and/or acetabulum fracture. Nevertheless, it is contemplated that the bone fastening system of the present invention can be employed with other applications for the treatment of fractured bones.

In a further aspect, the present invention provides a surgical kit comprising at least one bone fastening system described above, a wire positioner, a guide wire, and an insertion tool for fastening the screw component of the bone fastening system. Preferably, the surgical kit further comprises one or more dilatator(s) to facilitate insertion of the bone fastening system. The number of individual components within this set can of course be varied as desired.

For inserting or removing the screw component in or from the bone, an insertion tool with an engagement surface corresponding to the torque receiving surface of the screw component is provided. To this end, the torque receiving surface on the screw head and the corresponding engagement surface on the insertion tool are preferably matched to one another as precisely as possible to avoid that the tool has too much play and might damage the torque receiving surface.

The insertion tool is preferably cannulated such that it can be advanced over a guide wire with the screw component in the extension of the central longitudinal axis thereof.

In a preferred embodiment, the guide wire positioner comprises a beveled tip. As such, rotation of the guide wire positioner around the beveled tip allows for fine adjustment of the entry point for the placement of the components of the bone fastening system.

It is further preferred that a threaded guide wire, i.e. a guide wire having at least a threaded portion, is used for threading into the bone. The thread also allows for redirecting the guide wire in case of misplacement.

Radio markers may be included on the components of the kit, in particular the bone fastening system and/or the guide wire for identification under x-ray, fluoroscopy, CT or other imaging techniques.

In a further aspect, the present invention generally relates to a method for accurate stabilization of an articulated joint or a bone fracture. In particular, a method is provided for inserting a bone fastening system described above into the pelvic ring, e.g. for posterior percutaneous pelvic ring fixation.

In line with the method of the present invention one or more bone fastening systems described above are placed percutaneous and thereby allow for minimally invasive stable fixation of fractures and disruptions of the posterior pelvic ring.

Due to the minimally-invasive approach, less soft tissue damage is caused compared to conventional open reduction and plate fixation. The subcutaneous positioning of the bone fastening system is isolated from an intra-abdominal operation site; thereby the risk of bacterial colonisation and consecutive soft tissue infection is minimized. In addition, the percutaneous fixation method of the present invention avoids any contact to a possible laparotomy site and requires no extracorporal components at all.

In contrast to often used CT-guided/computer-navigated screw positioning techniques, the method of the present invention uses fluoroscopy, which provides a straightforward, thus less time-consuming, and inexpensive approach to intraoperative visualization.

The method of the present invention is generally performed with the patient in supine or prone position and closed reduction is preferably maintained by lateral compression. Prone positioning is preferred for heavier patients as it reduces the burden on the lung and respiratory system, whereas supine positioning allows an off-set from the table to ease the insertion of the bone fastening system.

According to the present invention, the following steps are performed:

With use of fluoroscopy, the first step is to mark the entry points for the bone fastening system, which—for placement of the S1 screws, are in the center plane between cranial and caudal endplate, preferably a few millimeters dorsally of the vertebral body's posterior margin in the lateral view. The entry points for S2 screws are in the middle of the S2 body. The use of fluoroscopic systems is known to a person skilled in the field of minimally invasive surgery.

"S1-S5" stand for the sacral vertebrae, numbered in descending order, which are the next lower succeeding five vertebrae below the lumbar vertebrae. Thus, S1 stands for the first sacral vertebra. Fused sacral vertebrae S1-S5 form the sacrum.

In the next step, skin incisions are performed. Blunt dissection may be used through the soft tissues, i.e. skin, fascia and muscle tissue. The location of the incision is dependent on the chosen procedure. For disrupted sacroiliac (SI) joint, the entry point is chosen preferably half way between the S1 endplate and the S2 endplate, close from the posterior border to the vertebral body.

Following the skin incisions a guide wire positioner, a trocar for instance, is then introduced, preferably in contact with the outer table of the iliac wing. Keeping the guide wire positioner in place, a guide wire is then inserted into the bone through the outer cortex of the ilium, by using a drill if applicable. Placement of the guide wire is preferably monitored and verified by fluoroscopic imaging. In this regard, fluoroscopy inlet, outlet and lateral view are preferably used to monitor the advancement of the guide wire across the SI joint or fracture. The use of fluoroscopic systems are known to a person skilled in the art of minimally invasive surgical procedures. It goes without saying that also other imaging techniques such as MRI, CT, ultrasound, radiography or X-ray may be used. An advantage of fluoroscopic systems is that, in comparison to general radiography where a static X-ray or an X-ray picture is provided, fluoroscopy offers a dynamic X-ray, or X-ray movie. Fluoroscopy is therefore particularly well suited for monitoring and verifying accurate placement of implant devices at the appropriate implant site.

In the next step, fascia and muscle tissue are subsequently dilated to allow for visualization and for creating a surgical pathway to the bone surface for implantation of components of the bone fastening system. Two dilators are preferably used sequentially to gently prepare a pathway in the muscle layer for the insertion of a working channel tube. In one example, 22-mm tube (12 cm in length) is used.

The working channel tube and/or the guide wire positioner preferably comprise an off-set handle for facilitating holding the tube in place without the hands holding the instruments obstructing the view. Alternatively, the working channel tube can be attached to the table via a flex arm.

Upon removal of the dilators (while leaving the guide wire and the working channel tube in place) a drill bit may be advanced over the guide wire to prepare a bore in the bone for insertion of the screw component of the bone fastening system. In an exemplary embodiment a 2.9 mm guide wire is used with a 5 mm drill bit. Depending on the bone density, drilling of a bore is not always necessary. For SI-joint fixation it is recommended to drill until the drill bit crosses the $3^{rd}$ cortical of the SI-joint. After drilling, the drill bit is subsequently removed, leaving the guide wire firmly in place.

The bone fastening system is then inserted over the guide wire, placed to the bone surface and advanced into the bone under fluoroscopic guidance.

In a preferred embodiment, the screw component is advanced into the bone by means of a screwdriver. To this end, the screwdriver preferably comprises a quick-connect handle with the selected bone screw length. The required length of the screw component can be measured by the use of a depth gauge, for instance, which is slid over the guide wire into the working channel tube.

Upon completion of the procedure, the surgical instruments, assemblies and non-implant components of the spinal implant system are removed from the surgical site and the incision is closed.

In a preferred embodiment the method of the present invention involves simultaneous placement of bone fastening systems in S1 and S2.

BRIEF DESCRIPTION OF THE DRAWINGS

The present invention is further illustrated by way of the attached figures which are described in detail in the following section and of which

DETAILED DESCRIPTION

To differentiate, corresponding features shown in different figures, i.e. features that are structurally identical or provide the same function, are each provided hereinafter with a common reference sign in the range of 1-99. In addition, reference signs in the 100s are provided to indicate the number of the respective figure. For example, a feature X shown in FIGS. 1A, 1B, 2 and 7 will be indicated with the reference number 1 in FIG. 1A, reference number 101 in FIG. 1B, reference number 201 in FIG. 2, and reference number 701 in FIG. 7.

Figure 1A:
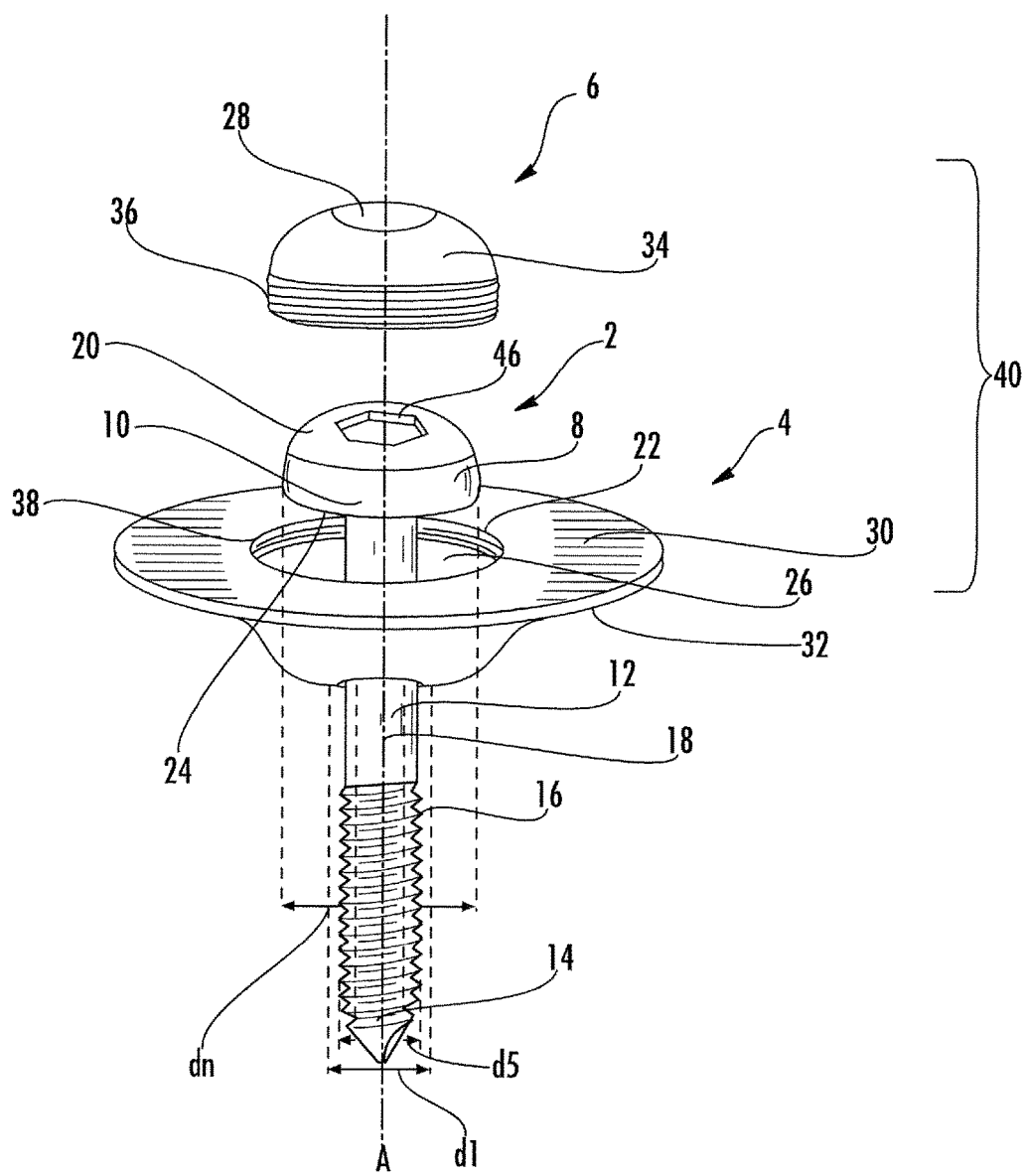
FIG. 1A shows a perspective view of a first embodiment of a bone fastening system according to the present invention with a holding component in the form of a cap.

The bone fastening system shown in FIG. 1A consists of metal, for example titanium or a titanium alloy, and includes a cannulated screw component 2, a seating component 4 and a holding component 6. The screw component 2 has a screw head 8 arranged in the region of a proximal end 10 of the screw component 2, and an elongate screw shaft 12 extending from the screw head 8 along a central longitudinal axis A towards a distal end 14 of the screw component 2.

In the embodiment shown in FIG. 1A, the elongate screw shaft 12 is cylindrically shaped and of constant diameter. The screw shaft 12 has an outer thread 16 for screwing the screw component 2 into a bone. The screw shaft 12 shown is only partially threaded; however, also fully threaded shafts are possible. Both the screw shaft 12 and the screw head 8 are substantially circular cylindrical. The screw shaft 12 is narrower, but much longer, than the screw head 8.

The cannulated screw component 2 comprises a central bore 18 extending the entire length of the screw component 2, i.e. through the screw head 8 and the screw shaft 12, along the longitudinal axis A. The screw head 8 comprises a proximal surface 20 on a front side facing the proximal end 10 and a distal surface 22 on a back side facing the distal end 14. A portion of the distal surface 22 forms a contact surface 24. A torque receiving surface 46 is formed in a recess in the proximal surface 10 of the screw head 8, the recess runs in a plane parallel to the longitudinal axis A and has a hexagonal cross-section in the radial plane. Thus, the torque receiving surface consists of six plane sections running parallel to the central axis A of the screw component 2 and being distributed uniformly in the circumferential direction such that they form three pairs of diametrically opposed sections. The torque receiving surface is intended to receive torque from an insertion tool (not shown).

Figure 1B:
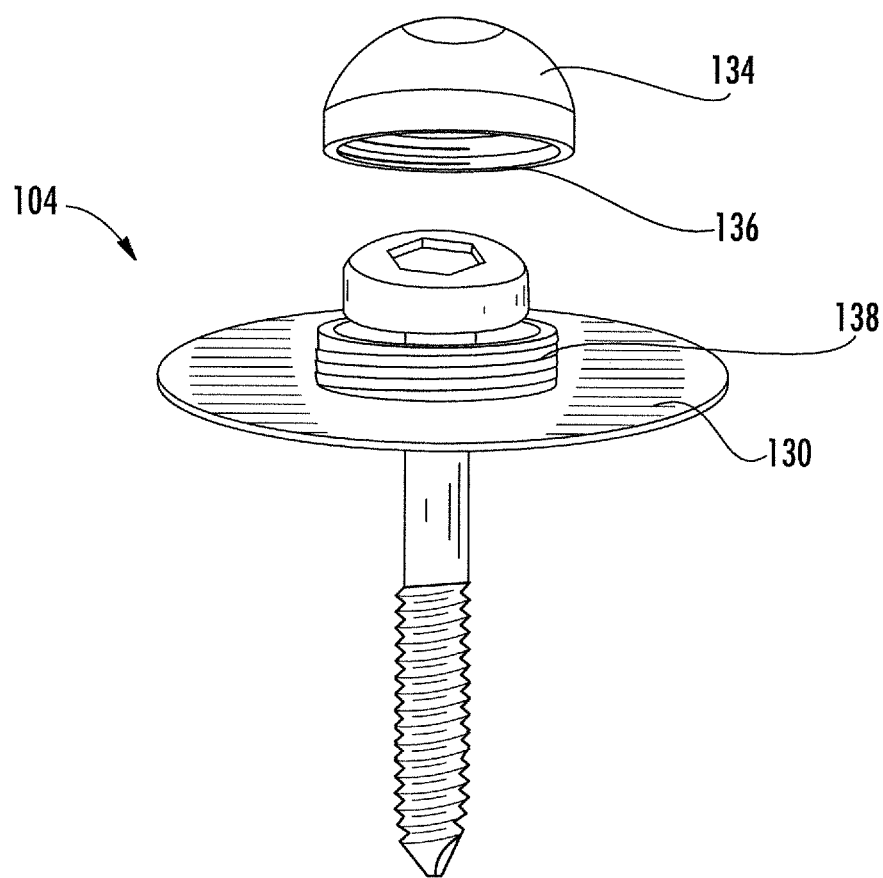
FIG. 1B shows a perspective view of an alternative embodiment of the bone fastening system with a holding component in the form of a cap.

The seating component 4 comprises a central opening 26, a seating surface 30 and a bottom surface 32. The seating component is in a circular shape. The central opening 26 has an opening diameter ($d_1$) which is larger than the maximum diameter ($d_s$) of the screw shaft 12 and which is smaller than the maximum diameter ($d_h$) of the screw head 8. The seating surface 30 is intended for abutting against the contact surface 24 and the bottom surface 32 is intended for abutting against the bone when the bone fasting system is in a fully engaged state. The seating component 4 may be disc-shaped as shown in FIG. 1B or may have a shape of a "soup plate", i.e. a deep, concave plate with a wide rim.

In the embodiment shown in FIG. 1A, the holding component 6 is in form of a cap 34 that is releasably connectable to the seating component 4 by means of a threaded section 36 that engages with a correspondingly threaded section 38 of the seating component 4. The seating component 4 and the end cap 34 can thereby be screwed together, which provides a straight-forward and strong connection.

The shape and dimensions of the cap 34 are adapted to the outer contour and size of the screw head 8. In particular, the inner contour of the cap 34 and the outer contour of the screw head 8 are matched such that they have e.g. a common inclination. The cap 34 also comprises a central opening 28, which allows for the insertion of surgical instruments, e.g. a screwdriver, for engaging with the screw component 2.

Together with the seating component 4, the holding component 6 defines an accommodation portion 40 for accommodating the screw head 8 such that the screw component 2 and the seating component 4 are connected in a non-detachable manner while at the same time allowing axial rotation of the seating component 4 with respect of the screw component 2. In particular, the screw head 8 can freely rotate around the longitudinal axis A relative to the seating component 4.

FIG. 1B shows an alternative embodiment of the bone fastening system shown in FIG. 1A. Contrary to the one presented in FIG. 1A, the cap 134 comprises an internal threaded section 136 that engages with a correspondingly threaded section 138 of the seating component 104. The threaded section 138 has in the shown embodiment a collar-like shape that protrudes from the seating surface 130 of the seating component 104. The seating component 104 and the end cap 134 can thereby be screwed together, which provides a straight-forward and strong connection.

Figure 2:
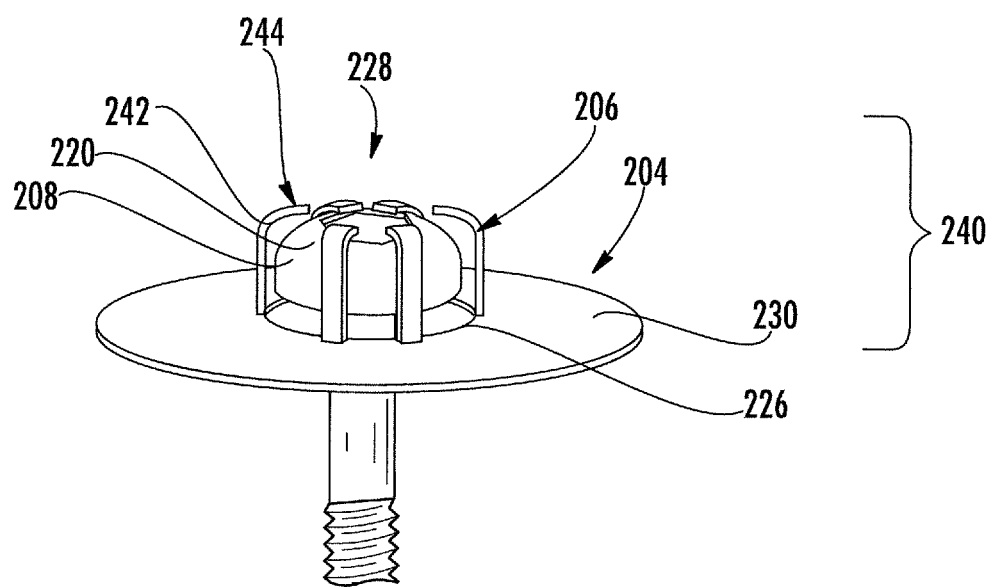
FIG. 2 shows a perspective view of a further embodiment of a bone fastening system according to the present invention with a holding component in the form of resiliently deformable fingers.

In the embodiment shown in FIG. 2, the holding component 206 consists of a multiplicity of integrally formed elastically deformable fingers 242, which are evenly distributed around the central opening 226 formed in the seating surface 230 of the seating component 204 and project away from the latter. To match the outer contour of the screw head 208 the fingers 242 are slightly arc-shaped and tilted inwards, such that the tips 244 of the fingers 242 define the central opening 228 of the holding component 206. The central opening 228 of the holding component 206 has an opening diameter smaller than the maximum diameter of screw head 208, such that the holding component 206 engages behind the proximal surface 220 of the screw head 208 as the screw head 208 is pushed through the central opening 228 of the holding component 206 during assembly. During the insertion of the screw head 208 into the accommodation portion 240, the fingers 242 are deflected radially outwards to provide sufficient access for the screw head 208 to be received within the accommodation portion 240. Then, the fingers 242 spring back inwards such that at least the finger tips 244 are substantially co-planar with the proximal surface 220 of the screw head 208.

Figure 3:
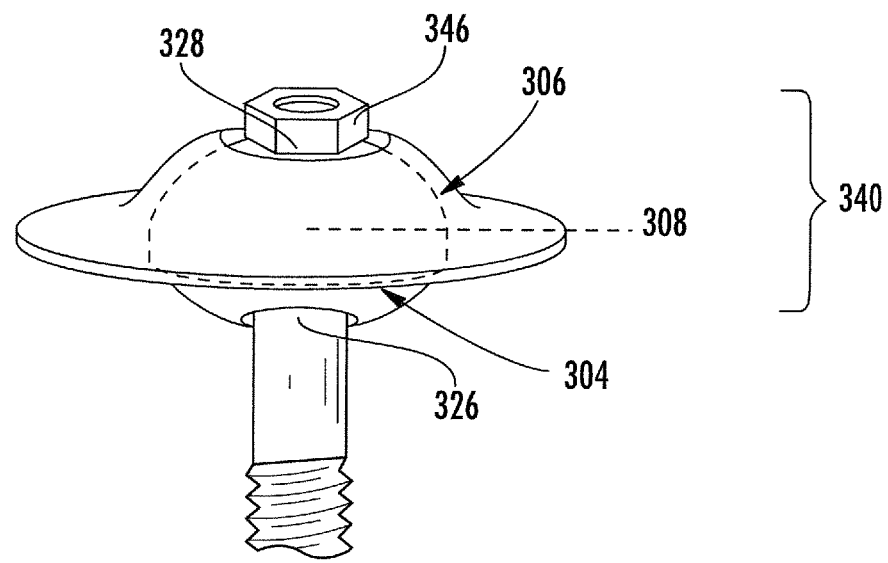
FIG. 3 shows a perspective view of a still further embodiment of a bone fastening system according to the present invention.
Figure 4:
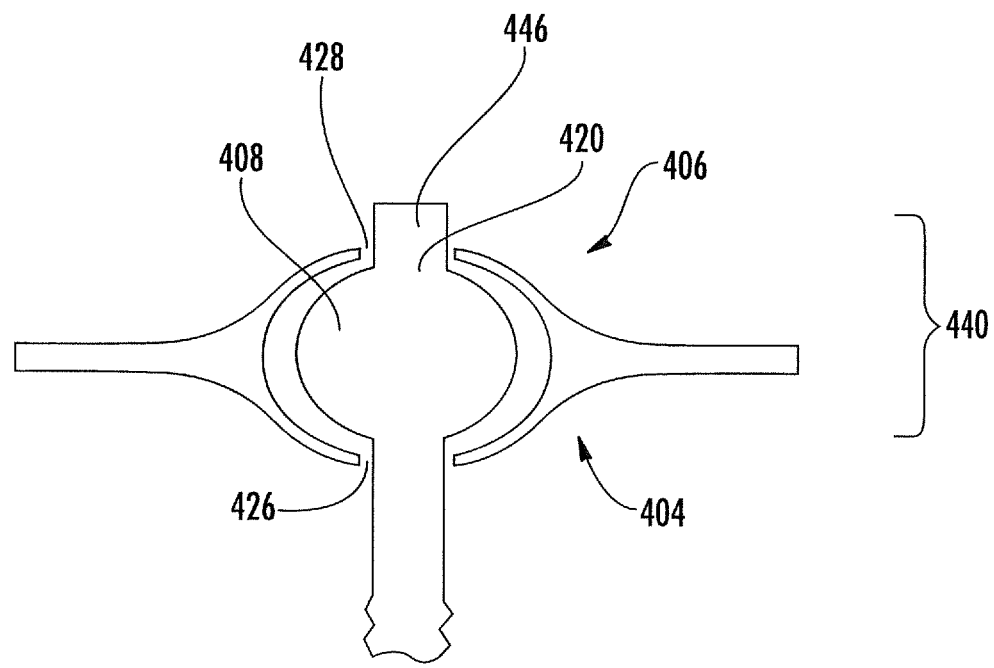
FIG. 4 shows a side view of the bone fastening system shown in FIG. 3 in the longitudinal central section through a sectional plane, which runs in the axial direction of the bone fastening system.

In the embodiment shown in FIGS. 3 and 4, the seating component 4 and the holding component 306, 406 are integrally formed and are elastically deformable at least in a region around the central opening 328, 428 in a radially outward direction. This allows for insertion of the screw head 308, 408 from below through the central opening 326, 426 of the seating component 304, 404 and/or from above through the central opening 328, 428 of the holding component 306, 406 into the accommodation portion 340, 440. The screw head 308, 408 further comprises a torque receiving surface 346, 446 intended to receive torque from an insertion tool. The torque receiving surface 346, 446 is formed as a post protruding from the proximal surface 320, 420 of the screw head 308, 408, the post having a polygonal cross-section in the radial plane.

In the embodiments shown in FIGS. 1 to 4, the bone fastening system is designed such that, when it is brought into the fully engaged state, the seating component 4 is fixed to the screw component 2 in a manner to prevent relative longitudinal displacement. Thus, at least part of the contact surface 24 of the screw head 8 abuts against the seating surface 30 and the holding component 6 at least partly abuts the proximal surface 20 of the screw head 8.

The seating component 4 may further comprise protrusions extending from the bottom surface 32. The protrusions may be in the form of teeth, serrations, grooves, or ridges and are intended for grabbing into the bone, holding the bone fastening system in place. This prevents migration of both, the screw component 2 and the seating component 4.

Figure 5A:
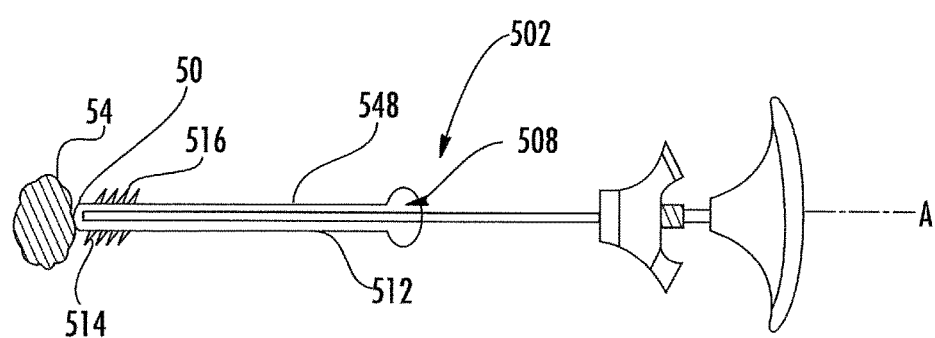
FIG. 5A shows a perspective view of an embodiment of a screw component in which an axial channel extends along the longitudinal axis through the screw head and the screw shaft.
Figure 5B:
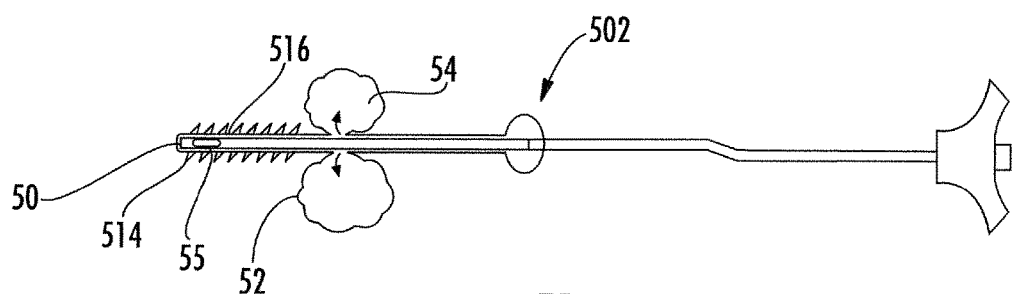
FIG. 5B shows a perspective view of a further embodiment of the screw component shown in FIG. 5A.

FIGS. 5A and 5B show an embodiment of the bone fastening system in which an axial channel 548 extends along the longitudinal axis A through the screw head 508 and the screw shaft 512 and opens out into the exterior through a primary fenestration 50 arranged at the distal end 514 of the screw component 502. This allows for the injection of bone cement 54 through the screw component 502 into the cancellous bone to augment the bone around the screw threads 516 in order to increase the strength of fixation of the screw in the bone and to fill the fracture void.

In the embodiment shown in FIG. 5B, the axial channel further opens out into at least one secondary fenestration 52 arranged offset from the distal end 514 at a predetermined height of the screw shaft 512. Through the secondary fenestration 52 injection of bone cement 54 in the area around the screw threads 516 is facilitated and allows simple, accurate and timely cement augmentation after insertion. The primary fenestration 50 at the distal end 514 of the screw component 502 is blocked by a plug 55 such that the bone cement 54 is forced out through the secondary fenestration 52.

Figure 6:
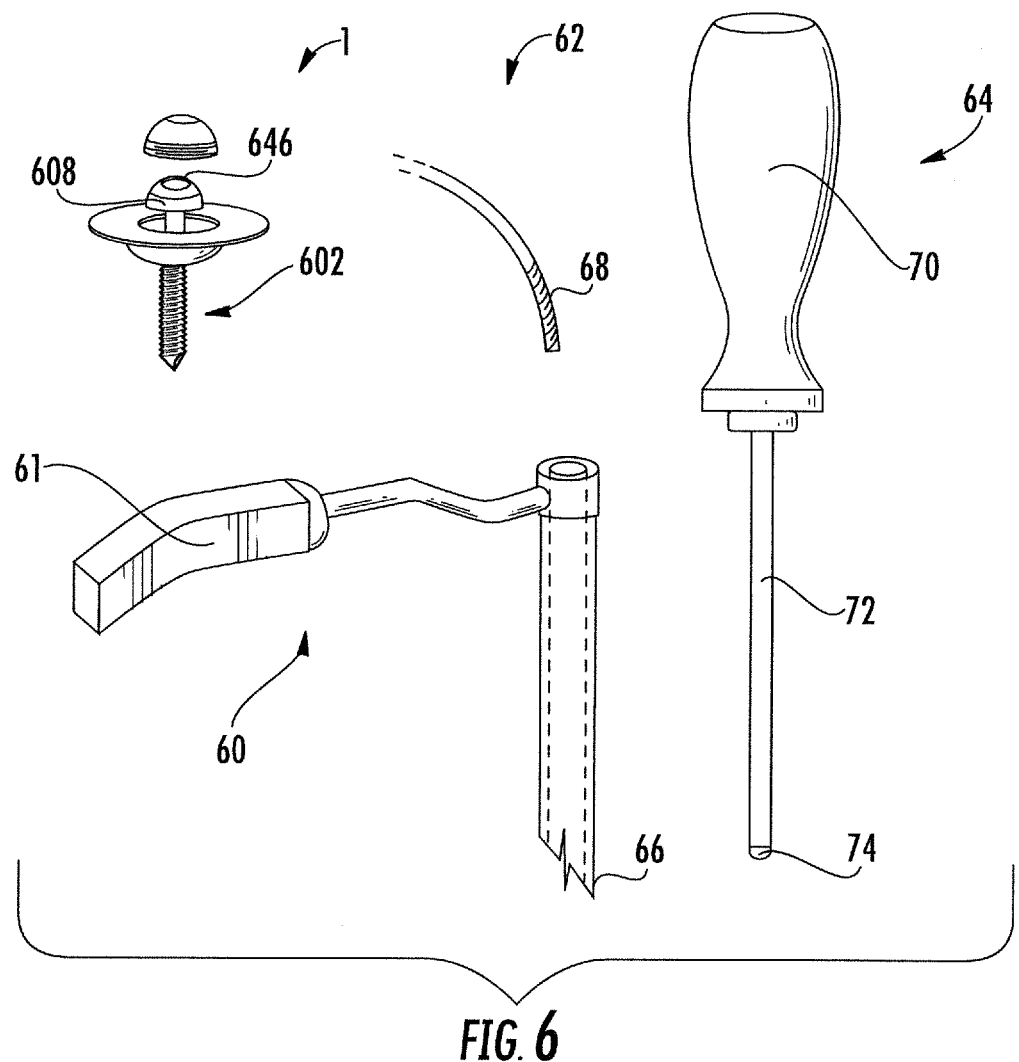
FIG. 6 shows a perspective view of an embodiment of a kit comprising a bone fastening system of the present invention, a guide wire positioner, a guide wire, and an insertion tool for fastening the screw component of the bone fastening system.

FIG. 6 shows a perspective view of a kit according to the present invention, comprising a bone fastening system 1, a guide wire positioner 60, a 2.9 mm guide wire 62, and an insertion tool 64 for fastening the screw component 2 of the bone fastening system. In the shown embodiment, the guide wire positioner 60 comprises a beveled tip 66. As such, rotation of the guide wire positioner 60 around the beveled tip 66 allows for fine adjustment of the entry point for the placement of the components of the bone fastening system. The guide wire positioner 60 further comprises an offset handle 61 for facilitating holding the guide wire positioner 60 in place without the hands holding the instruments obstructing the view.

The guide wire 62 comprises a threaded portion 68 for threading the guide wire 62 into the bone. The thread 68 also allows for re-directing the guide wire 62 in case of misplacement. The insertion tool 64 is cannulated such that it can be advanced over the guide wire 62 with the screw component 602 in the extension of the central longitudinal axis thereof.

The insertion tool 64 shown in FIG. 6 is a commercially available screwdriver comprising a hexalobular external driving feature or external torx. Alternatively, depending on the embodiment of the torque receiving surface of the screw component, it would also be possible to use a different commercially available insertion tool with a tip matched to the torque receiving surface of the screw component. The insertion tool 64 comprises a grip part 70, which can be held by a user, and a working part 72 connected thereto and comprising a tip 74. In analogy to the guide wire positioner 60, the insertion tool 64 can be provided with an offset handle instead of grip part 70. The tip 74 is used to temporarily engage in the screw component 602 and to transfer torque thereto. To this end, the tip 74 is introduced into the hexagonal-shaped recess 646 in the head 608 of the screw component 602.

Figure 7:
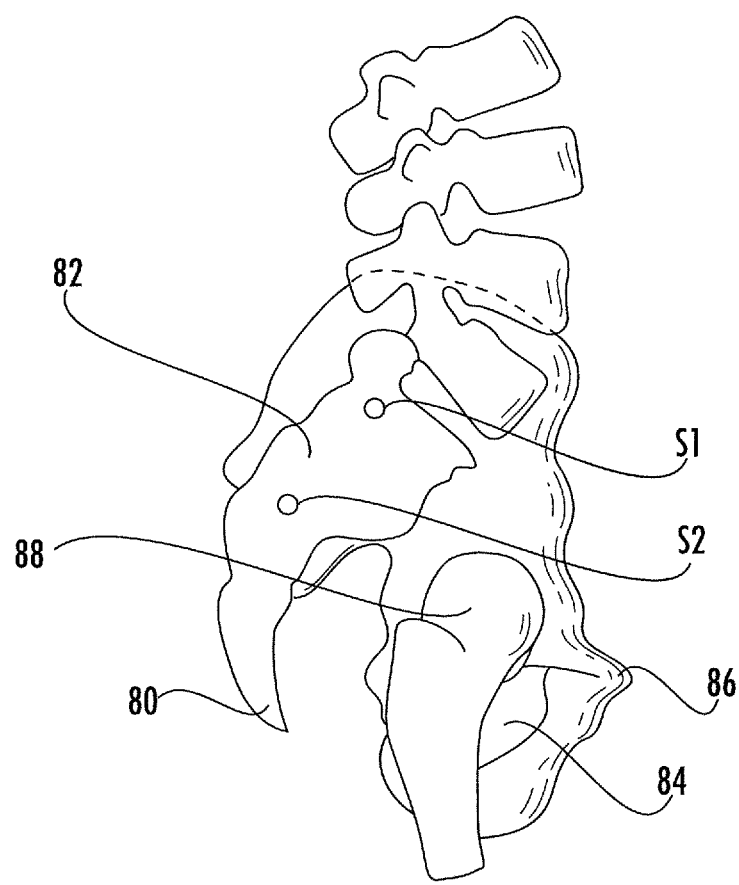
FIG. 7 shows a lateral view of a human pelvis with marked entry points for inserting the bone fastening system.

FIG. 7 shows a lateral view of human pelvis with marked entry points S1 and S2 for inserting the bone fastening system for iliosacral screw fixation. The lower regions of the spinal column comprising the coccyx 80, fused sacral vertebrae forming the sacrum 82, obturator foramen 84, pubic bone 86, and femoral head 88 are depicted. The sacral vertebrae S1 and S2 articulate with the pelvis via the sacroiliac joint. It is to be noted that the exact location of the incisions at the entry points S1 and S2 is dependent on the chosen procedure.

The invention claimed is:
1. A bone fastening system comprising:
a single cannulated screw component;
a seating component; and
a holding component;
wherein the single cannulated screw component comprises
a screw head adjacent a proximal end of the single cannulated screw component, and
an elongate screw shaft extending from the screw head along a longitudinal axis towards a distal end of the single cannulated screw component,
the screw head comprising a proximal surface on a front side facing the proximal end and a distal surface on a back side facing the distal end, at least a portion of said distal surface forming a contact surface,
wherein the seating component is disc-shaped and comprises a central opening having an opening diameter larger than a maximum diameter of the elongate screw shaft and smaller than a maximum diameter of the screw head, said seating component comprising
a seating surface to abut against the contact surface and
a bottom surface to abut against a bone when the bone fasting system is in a fully engaged state,
wherein the holding component cooperates with the seating component and defines an accommodation portion for accommodating the screw head such that the single cannulated screw component and the seating component are connected in a non-detachable manner while at the same time allowing axial rotation of the seating component with respect of the single cannulated screw component.

2. The bone fastening system according to claim 1, wherein the holding component comprises a holding surface, which at least partially overlaps with the proximal surface of the screw head.

3. The bone fastening system according to claim 1, wherein the holding component defines a central opening having an opening diameter smaller than the maximum diameter of the screw head.

4. The bone fastening system according to claim 3, wherein the seating component comprises elastically deformable material at least adjacent the central opening of the seating component to allow changing the opening diameter of the seating component; and wherein the holding component comprises elastically deformable material at least adjacent the central opening of the holding component to allow temporarily changing the opening diameter of the holding component.

5. The bone fastening system according to claim 1, wherein the holding component comprises an end cap that is releasably connected to the seating component.

6. The bone fastening system according to claim 5, wherein the end cap comprises a threaded section for engagement with a correspondingly threaded section of the seating component.

7. The bone fastening system according to claim 1, wherein when the bone fastening system is brought into the fully engaged state, the seating component is fixed to the single cannulated screw component in a manner to prevent relative longitudinal displacement.

8. The bone fastening system according to claim 1, wherein the single cannulated screw component comprises an axial channel extending along the longitudinal axis through the screw head and the elongate screw shaft, the axial channel opening out into an exterior through a primary fenestration arranged at the distal end of the single cannulated screw component.

9. The bone fastening system according to claim 8, wherein the axial channel further opens out into at least one secondary fenestration arranged offset from the distal end at a predetermined height of the elongate screw shaft.

10. The bone fastening system according to claim 1, wherein the elongate screw shaft has a diameter in a range of 7.0 to 8.0 mm.

11. The bone fastening system according to claim 1, wherein the single cannulated screw component has a length in a range of 20 to 200 mm.

12. A method for using a bone fastening system comprising a single cannulated screw component, a seating component, and a holding component, the single cannulated screw component comprising a screw head adjacent a proximal end of the single cannulated screw component, and an elongate screw shaft extending from the screw head along a longitudinal axis towards a distal end of the single cannulated screw component, the screw head comprising a proximal surface on a front side facing the proximal end and a distal surface on a back side facing the distal end, at least a portion of said distal surface forming a contact surface, the seating component being disc-shaped and having a shape of a concave plate with a planar annular rim, said seating component comprising a central opening having an opening diameter larger than a maximum diameter of the elongate screw shaft and smaller than a maximum diameter of the screw head, said seating component further comprising a seating surface to abut against the contact surface and a bottom surface to abut against a bone when the bone fasting system is in a fully engaged state, the bone fastening system further comprising a holding component cooperating with the seating component and defining an accommodation portion for accommodating the screw head such that the single cannulated screw component and the seating component are connected in a non-detachable manner while at the same time allowing axial rotation of the seating component with respect of the single cannulated screw component, the method comprising:

treating of a pelvic pathology.

13. The method according to claim 12 wherein the treating comprises treatment of a degenerative disease of an iliosacral joint requiring at least one of stabilization and fracture management of a pelvic ring, an iliosacral joint disruption and associated pelvic fracture, an osteoporotic fracture of a sacrum, an acetabulum fracture.

14. The bone fastening system according to claim 1, wherein the seating component has a shape of a concave plate with a planar annular rim.

* * * * *